United States Patent [19]

Hamey

[11] Patent Number: 4,626,249
[45] Date of Patent: Dec. 2, 1986

[54] FEMALE STANDING URINATION AID

[76] Inventor: Oliver R. Hamey, 725 N. Grant, Liberal, Kans. 67901

[21] Appl. No.: 721,676

[22] Filed: Apr. 10, 1985

[51] Int. Cl.[4] .............................................. A61F 5/44
[52] U.S. Cl. .................................. 604/329; 128/761; 4/144.4
[58] Field of Search ............................... 604/327–331, 604/354; 128/760–763, 767, 127–131; 4/144.1–144.4; 141/337, 338

[56] References Cited

U.S. PATENT DOCUMENTS

| | | | |
|---|---|---|---|
| 1,382,033 | 6/1921 | Wallace | 128/129 |
| 4,296,502 | 10/1981 | Bortle | 128/761 |
| 4,486,191 | 12/1984 | Jacob | 604/330 |
| 4,528,703 | 7/1985 | Kraus | 604/329 |

FOREIGN PATENT DOCUMENTS 117023  5/1943  Australia ........................... 604/330

*Primary Examiner*—C. Fred Rosenbaum
*Assistant Examiner*—Mario Costantino
*Attorney, Agent, or Firm*—Harvey B. Jacobson

[57] ABSTRACT

An elongated horizontal conduit is provided having one open end and an upwardly opening and upwardly projecting receiver at its other end. The receiver is elongated longitudinally of the conduit and includes a pair of opposite side walls interconnected at their opposite ends by integral end wall portions. The side walls closely oppose each other and control structure is provided whereby the mid-portions of the upper marginal edges of the side walls may be bowed outwardly. The control structure is operable from adjacent the open end of the conduit and the latter functions not only to drain off liquids received by the receiver, but also as a handle for properly positioning the receiver relative to a point of discharge of liquid to be received by the receiver.

8 Claims, 5 Drawing Figures

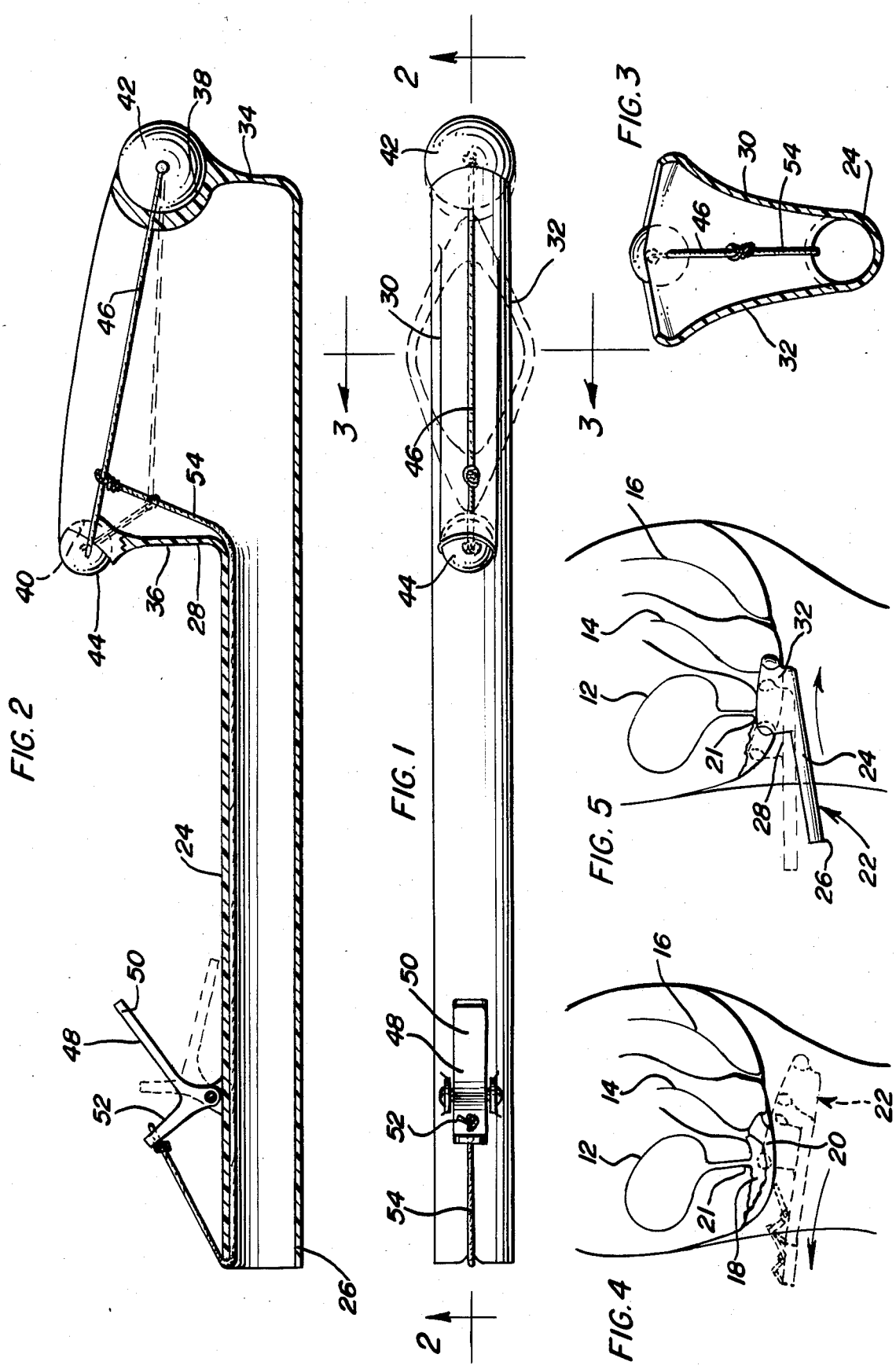

FEMALE STANDING URINATION AID

BACKGROUND OF THE INVENTION

1. Field of the Invention

This invention relates to an apparatus specifically designed to assist a female human in voiding urine while standing and includes structure whereby proper positioning of the urination aid relative to the user for proper operation of the aid may be readily accomplished.

2. Description of Related Art

Various different forms of female urination aids as well as urine collecting devices adapted for use on females heretofore have been provided. Examples of these previously known devices are disclosed in U.S. Pat. Nos. 1,407,872, 1,510,973, 3,613,122, 4,023,216, 4,194,508, 4,270,539 and 4,296,502.

SUMMARY OF THE INVENTION

The urination aid of the instant invention includes an elongated horizontal conduit open at one end and including an upwardly opening receiver at the other end opening downwardly into the conduit. The receiver is elongated longitudinally of the conduit and includes a pair of opposite side walls which project upwardly from opposite sides of the conduit and are inconnected at their opposite ends by end wall portions. The side walls closely oppose each other and an elongated flexible tension member extends between and is anchored relative to the upper marginal portions of the end wall portions. Further, structure, operable from the open end of the conduit, is provided for downwardly deflecting a longitudinal mid-portion of the tension member to cause the end wall portions to be displaced toward each other and the side walls to be outwardly bowed. In addition, the end wall portion remote from the open end of the conduit includes a bulbous upper end portion which is adapted to be seated in the outer end of the vaginal canal of the user.

The main object of this invention is to provide an aid for women to be used in urinating while standing.

Another object of this invention is to provide a urination aid for women constructed in a manner whereby the urine receiver portion of the aid may be readily maneuvered into correct position between the labia minora immediately forward of the vaginal canal so as to directly receive urine from the external urethral orifice.

Still another important object of this invention is to provide a urination aid in accordance with the preceding objects and which will conform to conventional forms of manufacture, be of simple construction and easy to use so as to provide a device that will be economically feasible, long lasting or disposable and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWING

FIG. 1 is a top plan view of the urination aid with outwardly bowed and flexed positions of the side walls of the receiver portion of the aid illustrated in phantom lines;

FIG. 2 is a longitudinal vertical sectional view taken substantially upon the plane indicated by the section line 2—2 of FIG. 1;

FIG. 3 is a transverse vertical sectional view taken substantially upon the plane indicated by the section line 3—3 of FIG. 1 and with the side walls of the receiver portion of the invention in outwardly bowed and flexed conditions;

FIG. 4 is a schematic view of the urogenital organs of a female in vertical section and with the aid of the instant invention illustrated in phantom lines in position preparatory to proper placement of the aid to receive urine therein; and FIG. 5 is a schematic view similar to FIG. 5 but illustrating the aid in its operative position in solid lines and in an intermediate position of proper positioning in phantom lines.

DESCRIPTION OF THE PREFERRED EMBODIMENT

Referring now more specifically to the drawings the numeral 10 generally designates the female body, see FIGS. 4 and 5 including the bladder 12, the vagina 14 and the rectum 16. Also, illustrated in FIG. 4 are the labia minora 18 and labia major 20. In addition, the external urethral orifice 21 is illustrated.

Referring now more specifically to FIGS. 1, 2 and 3, the urination aid of the instant invention is referred to in general by the reference numeral 22 and includes a tubular conduit 24 open at one discharging end 26 thereof and to provide it with an upwardly projecting receiver 28 at its inlet end.

The receiver 28 includes upwardly projecting opposite side walls 30 and 32 interconnected at corresponding ends by a rear end wall portion 34 and at their forward ends by a forward end wall portion 36. The upper extremities of the rear and front wall portions 34 and 36 define outwardly opening recesses 38 and 40 in which spherical anchors 42 and 44 are seated. An elongated flexible tension member 46 has its opposite ends anchored relative to the anchors 42 and 44 and is disposed in a substantially taut condition extending between the end wall portions 34 and 36 between the side walls 30 and 32.

A bell crank 48 is pivotally mounted from the upper side of the discharge end 26 of the conduit 24 and includes a first arm 50 for actuation by the user of the aid 22 and a second arm 52 to which one end of an elongated flexible pull member 54 is anchored. The pull member 54 extends from the second arm 52 into the discharge end 26 of the conduit, through the latter and upwardly into the upper portion of the receiver 28 and is anchored to a mid-portion of the tension member 46 spaced between the end wall portions 34 and 36. Thus, the bell crank 48 may be pivoted from the position thereof illustrated in solid lines in FIG. 2 of the drawings to the phantom line position thereof in FIG. 2 in order to downwardly deflect the longitudinal mid-portion of the tension member 46 and thus displace the upper portions of the end wall portions 34 and 36 toward each other. This will cause the upper marginal portions of the side walls 30 and 32 to become outwardly bowed in order to "open" the upper end of the receiver 28.

The receiver 28 is constructed of shape retentive but slightly resilient and deformable material and may be formed integrally with the conduit 24. In addition, the abutments 42 and 44 may be formed as integral portions of the end wall portions 34 and 36.

In order to properly position the aid 22 for urination there into with the aid positioned as illustrated in the solid lines in FIG. 5, the discharge end of the conduit 24 is grasped in either hand by the user and initially placed in the crotch area at least somewhat rearward of the vagina and with the abutment 44 registered with a forward extremity of the perineum. Then, with the conduit 24 disposed in a slightly forwardly and upwardly inclined position such as that illustrated in phantom lines in FIG. 4, the aid 22 is displaced forwardly in the direction of the arrow 56 whereby the abutment 44 will part not only the rear ends of the labia major but also the rear ends of the labia minora in order that the entire upper portion of the receiver 28 may be received between the labia minora. Thereafter, the forward end of the conduit 24 is slightly lowered and the aid 22 is displaced rearwardly in the direction of the arrow 58 to the solid line position of the aid illustrated in FIG. 10 with the abutment 42 seated against the rear of the vaginal opening.

When thus positioned the upper marginal edges of the side walls and end wall portions of the receiver 28 are seated between the labia minor and the user then presses downwardly on the arm 50 in order to exert a forward and downward pull on that portion of the pull member 54 disposed within the receiver 28 so as to downwardly deflect the attached portion of the tension member 46. This will cause the end wall portions 34 and 36 to be displaced toward each other and the upper marginal edges of the side walls 30 and 32 to be outwardly bowed and thus spread apart to more fully open that portion of the receiver registered with the outer urethral orifice 21. At this point, urination may commence and be carried out with total freedom from leakage.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A female standing urination aid including an elongated generally horizontal conduit having opposite ends, one end of said conduit being open and comprising a discharge end and the other end of said conduit comprising an inlet end and including means defining an upwardly projecting receiver opening downwardly into said other end, said receiver including closely opposing generally parallel opposite side walls extending longitudinally of said conduit and end wall portions extending between and connecting corresponding ends of said side walls, said side walls and end wall portions projecting at least slightly upwardly from said inlet end and being integrally formed of resilient and shape retentive material, manually operable receiver opening means operative from a point spaced along said conduit from said receiver toward said discharge end and connected to at least the end wall portion of said receiver furthest from said discharge end to relatively displace said end wall portions toward each other and thus reduce the spacing therebetween, said receiver being constructed in a manner such that at least the mid-portions of said side walls will bow so as to be outwardly convex and thus spread apart responsive to said end wall portions being relatively displaced toward each other, thereby opening said receiver for receiving liquid thereinto from above.

2. The urination aid of claim 1 wherein said receiver opening means includes a flexible substantially taut tension member extending between and having opposite end portions each anchored relative to a corresponding one of said end wall portions and deflection means for downwardly deflecting a mid-length portion of said tension member.

3. The urination aid of claim 2 wherein said deflection means includes an elongated flexible tension member having first and second ends and extending through said conduit and up into said receiver and having said first end anchored to the first mentioned tension member at a point spaced between said end wall portions.

4. The urination aid of claim 3 including manually operable pull means shiftably supported from said discharge end of said conduit and to which the second end of the second mentioned tension member attached.

5. The urination aid of claim 4 wherein said pull means includes a bell crank pivotally supported from said discharge end of said conduit.

6. The urination aid of claim 1 wherein said conduit comprises a tubular member.

7. The urination aid of claim 1 wherein said side walls and end wall portions include generally co-planar upper marginal portions disposed in a plane relative to which said conduit is downwardly inclined toward said discharge end.

8. The urination aid of claim 1 wherein said end wall portions include upper extremities defining generally partial spherical surfaces facing upwardly and outwardly in opposite directions from said receiver.

* * * * *